(12) United States Patent
Gorr et al.

(10) Patent No.: US 7,741,539 B2
(45) Date of Patent: Jun. 22, 2010

(54) TRANSFORMED PLANT CELL EXPRESSING FIVE MAMMALIAN PROTEINS INVOLVED IN SIALYLATION AND A PROTEIN INVOLVED IN GALACTOSYLATION

(75) Inventors: Gilbert Gorr, Freiburg (DE); Heike Launhardt, Freiburg (DE); Marta Rodriguez Franco, Freiburg (DE); Christian Stemmer, Freiburg (DE)

(73) Assignee: greenovation Biotech GmbH, Freiburg (DE)

( * ) Notice: Subject to any disclaimer, the term of this patent is extended or adjusted under 35 U.S.C. 154(b) by 0 days.

(21) Appl. No.: 11/995,191

(22) PCT Filed: Jul. 12, 2006

(86) PCT No.: PCT/EP2006/006831

§ 371 (c)(1),
(2), (4) Date: Jan. 9, 2008

(87) PCT Pub. No.: WO2007/006570

PCT Pub. Date: Jan. 18, 2007

(65) Prior Publication Data

US 2008/0201804 A1    Aug. 21, 2008

Related U.S. Application Data

(60) Provisional application No. 60/698,246, filed on Jul. 12, 2005.

(51) Int. Cl.
*A01H 5/00* (2006.01)
*C12N 15/82* (2006.01)

(52) U.S. Cl. .................. 800/298; 800/288; 435/419

(58) Field of Classification Search .............. None
See application file for complete search history.

(56) References Cited

FOREIGN PATENT DOCUMENTS

| EP | 1 510 584 A1 | | 3/2005 |
|---|---|---|---|
| WO | WO 00/52135 A2 | | 11/2000 |
| WO | WO 01/25456 A2 | | 5/2001 |
| WO | WO 2004/057002 | * | 7/2004 |
| WO | WO 2004/057002 A2 | | 7/2004 |
| WO | WO 2004/063370 A1 | | 7/2004 |
| WO | WO 01/31045 A1 | | 8/2004 |
| WO | WO 2004/071177 A2 | | 8/2004 |
| WO | WO 2005/090552 A2 | | 9/2005 |

OTHER PUBLICATIONS

Warner, T.G. Metabolic engineering glycosylation: biotechnology's challenge to the glycobiologist in the next millennium. (2000) in Carbohydrates in Chemistry and Biology, edited by Ernst, Hart, and Sanay; Wiley-VCH Weinheim; New York; pp. 1043-1064.*

Altmann et al., Glycoysylation of the capsid proteins of cowpea mosiac virus: a reinvestigation shows the absence of sugar residues, Journ. of General Virol. 81:1111-14 (2000).

Altschul et al., Basic local alignment search tool, J. Mol. Biol. 215:403-410 (1999).

Aumiller et al., A transgenic insect cell line engneered to produce CMP-sialic acid and sialyated glycoproteins, Glycobiology, IRL Press, GB 13(6):497-507 (2003).

Bakker et al., Galactose-extended glycans of antibodies produced by transgenic plants, Proc Natl Acad Sci USA 98(5) 2899-2904 (2001).

Baur et al., A fast and flexible PEG-mediated transient expression sytem in plants for high level expression of secreted recombinant proteins, Journ. of Biot 119:332-42 (2005).

Castilho et al, Constructiohn of a Functional CMP-Sialic Acid Biosynthesis Pathway in Arabidopsis, Plant Physiol 147:331-359 (2008).

Cohen et al., Functional expression in yeast of the *E.coli* plasmid gene coding for chloramphenicol acetyltransferase, Proc. Natl. Acad. Sci, USA 77(2):1078-82 (1980).

Girke et al., Identification of a novel D6-acyl-group desaturase by targeted gene disruption in *Physcomitrella patens*, The Plant Journal 15(1):39-48 (1998).

Gomord et al., Postranslational modification of therapeutic proteins in plants, Curr. Opin. in Plant Biol. 7:171-181 (2004).

Hara et al., Fluorometric high-performance liquid chromotagraphy of N-acetyl- and N-glycolylnueraminic acids and its applicatioan, Analytical Biochemistry 164:138-145 (1987).

Henikoff et al., Isolation of a gene from Drosophila by complementation in yeast, Nature 289:33-7 (1981).

Hollenberg, The expression of bacterial antibiotic resistance genes in the yeast *Saccharomyces cerevisiae*, (eds, K.N. Timms and A. Phuler) 1979.

Huether et al., Glyco-engineering of moss lacking plant-specific sugar residues, Plant Biology 7:292-299 (2005).

Hollenberg et al., Cloning with 2-um DNA vectors and expression of foreign genes in *Saccharomyces cerevisiae*, Curr. Topics Microbiol. Immunol. 96:119-144 (1982).

(Continued)

*Primary Examiner*—Cathy Kingdon Worley
(74) *Attorney, Agent, or Firm*—Biotech Beach Law Group PC; Raymond Wagenknecht

(57) ABSTRACT

The present invention relates to a method for producing heterologous glycosylated proteins in non-animal eukaryotic cells such as in transformed bryophyte, yeast, ciliate or algae cells. In particular, the method relates to a method for producing glycosylated proteins comprising animal glycosylation patterns—comprising sialic acid residues—, such as pharmaceutical proteins for use in mammals, e.g. humans, in bryophyte cells such as those of *Physcomitrella patens*, the genetic material required therefore, such as DNA and RNA, vectors, host cells, methods of introducing genetic material there into, and uses thereof. Furthermore, the present invention relates to novel polypeptides and proteins obtained by the method according to the invention. Moreover, the present invention provides a method of producing sialic acid or CMP-sialic acid in a transformed non-mammalian eukaryotic cell, tissue or organism.

13 Claims, No Drawings

OTHER PUBLICATIONS

Kaprivova et al., Functional knockout of the adenosine 5'-phosphate reductase gene in *Physcomitrella patens* revives an old route, Jour of Biol. Chem. 277(35):32195-32201 (2002.

Kaprivova et al, Targeted knockouts of *Physcomitrella* lacking plant specific immunogenic N-glycans, Plant Biotechnol. Journ. 2:517-523 (2004).

Ma et al., The production of recombinant pharmaceutical proteins in plants, Nature Reviews 4:794-805 (2003).

Maliekal et al., Identification of the sequence encoding N-acetylneraminate-9-phosphate phosphatase, Gylcobiology 16(2):165-172 (2006).

Mercereau-Puijalon et al., Synthesis of a chicken ovalbumin-like protein in the yeast *Saccharomyces cervisiae*, Gene 11:163-7 (1980).

Palacpac et al., Stable expression of human B1,4-galactosyltransferase in plant cells modifies N-linked glycosylation patterns, Proc. Natl. Acad. Sci. USA 96:4692-7 (1999).

Panthier et al., Cloned B-galactosidase gene of *E. coli* is expressed in the yeast *Saccharomyces cerevisiae*, Current Genetics 2:109-113 (1980).

Pearson et al., Rapid and sensitive sequence comparison with FASTP and FASTA, Methods in Enzymology 183:63-98 (Academic Press) (1990).

Reski et al., Induction of budding on chloronemata and caulonemata of the moss, *Physcomitrella patens*, using isopentenyladenine, Planta 165:354-8 (1985).

Reski et al., Genome analysis of the moss *Physcomitrella patens* (Hedw.) B.S.G., MOl. Gen. Genet. 244:352-9 (1994).

Reski et al., Development, Genetics and Molecular Biology of Mosses, Bioacta 111:1-15 (1998).

Reski et al., Molecular genetics of *Physcomitrella*, Planta 208:301-309 (1999).

Reutter et al., Production of a heterologous protein in bioreactor cultures of fully differentiated moss plants, Plant Tissue Culture and Biotechnology 2(3):142-147 (1996).

Rudolph et al., Studies on secondary metabolism of *sphagnum* cultivated in bioreactors, Crypt, Bot 6:67-73 (1992).

Schaefer, A new moss genetics: targeted mutagenesis in *Physcomitrella patens*, Annu. Rev. Plant Biol. 53:477-501 (2002).

Schaefer, Principles and protocols for the moss *Physcomitrella patens*, (May 2001), Institute of Ecology, Laboratory of Plant Cell Genetics, University of Lausanne.

Schaefer et al., The moss *Physcomitrella patens*, now and then, Plant Physiol. 127:1430-8 (2001).

Seveno et al., Glycoprotein sialylation in plants?, Nature Biotechnology 22(11) 1351-2 (2004).

Shah et al, Sialylated endogenous glyconguates in plant cells, Nature Biotechnology Online 10.1038/nbt912 (2003).

Smith et al., Comparison of Biosequences, Advances in Applied Mathematics 2:482-9 (1981).

Stemmer et al., Marker-free transformation of *Physcomitrella patens*, 7th Annual Moss International Conference, Freiburg, Germany (2004).

Strasser et al., Generation of *Arabidopsis thaliana* plants with complex N-glycans lacking beta 1,2-linked xylose and core alpha 1,3-linked fucose, FEBS Letters 561:132-6 (2004.

Strepp, Plant nuclear gene knockout reveals a role in plastid division for the homolog of the bacterial cell division protein FtsZ, an ancestral tubulin, PNAS 95:4368-73 (1998.

Viswanathan et al., Engineering intracellular CMP-sialic acid metabolism into insect cells and methods to enhance its generation, Biochemistry 44:7526-34 (2005).

Weise et al., Use of *Physcomitrella patens* actin 5' regions for high transgene expression: importance of 5' introns, Appl. Microbiol. Biotechnol. (2005).

Zeidler et al., Transgene expression in the moss ceratodon purpureus, J. Plant Physiol. 154:641-50 (1999).

Zeidler et al., Tetracycline-regulated reporter gene expression in the moss *Physcomitrella patens*, Plant Molec. Biol. 30:199-205 (1996).

* cited by examiner

TRANSFORMED PLANT CELL EXPRESSING FIVE MAMMALIAN PROTEINS INVOLVED IN SIALYLATION AND A PROTEIN INVOLVED IN GALACTOSYLATION

CROSS REFERENCE TO RELATED APPLICATIONS

This is a National Phase Application in the United States of America of International Patent Application No. PCT/EP2006/006831, filed Jul. 12, 2006, which claims priority to U.S. Provisional Patent Application No. 60/698,246 filed on Jul. 12, 2005. The entire disclosures of the above patent applications are herein incorporated by reference in their entirety.

BACKGROUND

The present invention relates to a method for producing heterologous glycosylated proteins in non-animal eukaryotic cells such as in transformed bryophyte, yeast, ciliate or algae cells. In particular, the method relates to a method for producing glycosylated proteins comprising animal glycosylation patterns—comprising sialic acid residues—, such as pharmaceutical proteins for use in mammals, e.g. humans, in bryophyte cells such as those of *Physcomitrella patens*, the genetic material required therefore, such as DNA and RNA, vectors, host cells, methods of introducing genetic material there into, and uses thereof. Furthermore, the present invention relates to novel polypeptides and proteins obtained by the method according to the invention. Moreover, the present invention provides a method of producing sialic acid or CMP-sialic acid in a transformed non-mammalian eukaryotic cell, tissue or organism.

Plants are appropriate organisms for the production of a wide range of recombinant proteins (Ma et al. (2003) Nat Gen 4, 794-805). In terms of pharmaceutical proteins for use in mammals, including humans, post-translational modifications, such as glycosylation, are often required. However, a problem encountered in eukaryotic cell systems which have been transformed with heterologous genes suitable for the production of protein sequences destined for use, for example, as pharmaceuticals in humans, is that the glycosylation pattern on such proteins often acquires a native pattern, that is, of the eukaryotic cell system into which the protein has been introduced: glycosylated proteins are produced that comprise non-animal, that is to say, for example, non-mammalian glycosylation patterns and these in turn may be immunogenic and/or allergenic if applied in animals, such as mammals, e.g. humans.

Compared to mammalian-derived glycoproteins, plant-specific glycoproteins contain two additional residues. In the past, the use of recombinant glycoproteins produced by plants was limited by the plant-specific N-glycosylation that is acquired on such proteins. In the case of bryophytes Koprivova et al. ((2004), Plant Biotechnol J 2, 517-523) and in the case of seed plants Strasser et al. ((2004) FEBS Lett. 561, 132-136)) succeeded in overcoming this limitation using different approaches. The plants generated in the two studies showed complex N-glycosylation lacking the above mentioned two plant-specific sugar residues.

Moreover, in plants glycoprotein terminal beta 1,4-galactose residues are not found, indicating that a beta 1,4-galactosyltransferase is not present in plants. Stable integration and expression of this enzyme in tobacco plants (Bakker et al. (2001) *Proc Natl Acad Sci* USA 98, 2899-2904), in tobacco BY2 cells (Palacpac et al. (1999) *Proc Natl Acad Sci* USA 96, 4692-4697) as well as in gametophytic haploid bryophytes (Huether et al. (2005) Plant Biol 7, 292-299) has been described. The recombinant human beta 1,4-galactosyltransferase was functional and proteins isolated from transgenic material exhibited terminal beta 1,4-galactose residues.

The present invention is concerned with the further improvement of existing methods in order to ensure that polypeptides and proteins with still further improved functionality in animals, such as mammals, are produced.

The most complex N-glycan structures present on mammalian proteins, including human proteins, contain sialic acids as terminal sugar residues. Although the presence of sialylated glycoconjugates in non-transgenic suspension cultured cells of *Arabidopsis thaliana* was described recently by Shah et al. ((2003) Nat Biotechnol 21, 1470-1471), these results are under discussion (Seveno et al. (2004) Nat Biotechnol 11, 1351-1353).

However, the prior art does not provide any information on whether sialylation also takes place in bryophytes and may enable recombinant expression of heterologous glyco-proteins having the desired N-glycan characteristics. In addition, no data are available in the prior art as to the pure existence of sialic acid in any bryophyte.

A pre-requisite for sialylation on N-glycans is the presence of activated neuraminic acid (CMP NeuAc). In mammals different enzymes are involved in the synthesis of NeuAc (sialic acid)—the precursor of CMP NeuAc. UDP-N-acetyl-glucosamine-2-epimerase/N-acetylmannosamine-6-kinase (genbank accession number: AF155663) is responsible for generating ManNAc-6P which is processed by N-acetyl-neuraminic acid phosphate synthase (genbank accession number: NM_018946) to NeuAc-9P. The enzyme responsible for processing NeuAc-9P into NeuAc is not described up to now. Activation of NeuAc takes place in the nucleus of mammalian cells. Responsible for generation of the activated sialic acid (CMP NeuAc) is the enzyme CMP-N-acetyl-neuraminic acid synthase (genbank accession number: NM_018686). The activated product has to be translocated from the nucleus into the Golgi apparatus—in this process the CMP-sialic acid transporter (genbank accession number: NM_006416) is involved. Finally, sialylation on N-glycans takes place by the transfer of CMP NeuAc on terminal sugar residues—e.g. 1,4 linked—galactose residues. For this purpose, expression of a sialyltransferase (e.g. alpha-2,6 sialyltransferase; accession number NM_003032, gene bank) has to be ensured. The bryophyte, *Physcomitrella patens*, a haploid non-vascular land plant, is able to be used for the production of recombinant proteins (WO 01/25456).

The life cycle of bryophytes is dominated by photoautotrophic gametophytic generation. The life cycle is completely different to that of higher plants wherein the sporophyte is the dominant generation and there are notably many differences to be observed between higher plants and bryophytes.

The gametophyte of bryophytes is characterised by two distinct developmental stages. The protonema which develops via apical growth, grows into a filamentous network of only two cell types (chloronemal and caulonemal cells). The second stage, called the gametophore, differentiates by caulinary growth from a simple apical system. Both stages are photoautotrophically active. Cultivation of protonema without differentiation into the more complex gametophore has been shown for suspension cultures in flasks as well as for bioreactor cultures (WO 01/25456). Cultivation of fully differentiated and photoautrophically active multicellular tissue containing only a few cell types is not described for higher plants. The genetic stability of the bryophyte cell system provides an important advantage over plant cell cultures. In cell cultures of higher plants the secondary metabolism is more differentiated and this results in differences in secondary metabolite profiles.

In addition, there are some important differences between bryophytes and higher plants on the biochemical level. Sulfate assimilation in *Physcomitrella patens* differs significantly from that in higher plants. The key enzyme of sulfate assimilation in higher plants is adenosine 5'-phosphosulfate reductase. In *Physcomitrella patens* an alternative pathway via phosphor-adenosine 5'-phosphosulfate reductase co-exists (Koprivova et al. (2002) J. Biol. Chem. 277, 32195-32201). This pathway has not been characterised in higher plants.

Further differences are reflected in the regeneration of the cell wall. Protoplasts derived from higher plants regenerate new cell walls in a rapid manner, independently of the culture medium. Direct transfer of DNA via polyethylene glycol (PEG) into protoplasts of higher plants requires pre-incubation at 4 to 10° C. to slow down the process of cell wall regeneration (U.S. Pat. No. 5,508,184). In contrast, cell wall regeneration of protoplasts derived from protonema of *Physcomitrella* is dependent on culture medium. Protoplasts can be cultivated without regeneration of the cell wall over long periods. Without the intention of being bound by theory, it appears that the secretion machinery of the protoplast, essential for cell wall regeneration and protein glycosylation, differs from that of higher plants. Moreover, *Physcomitrella patens* shows highly efficient homologous recombination in its nuclear DNA, a unique feature for plants, which enables directed gene disruption (Girke et al. (1998) *Plant J* 15, 39-48; Strepp et al. (1998) *Proc Natl Acad Sci* USA 95, 4368-4373; Koprivova (2002) J Biol Chem 277, 32195-32201; reviewed by Reski (1999) *Planta* 208, 301-309; Schaefer and Zryd (2001) *Plant Phys* 127, 1430-1438; Schaefer (2002) *Annu. Rev. Plant Biol.* 53, 477-501) further illustrating fundamental differences to higher plants.

It is an object of the present invention to provide a more efficient method of producing animal proteins comprising animal glycosylation patterns, and in particular, glycosylated human proteins comprising human glycosylation patterns thereon—containing sialic acid residues. It is a further object to provide an efficient process for the production of heterologous animal proteins comprising animal glycosylation patterns, particularly human proteins comprising human glycosylation patterns—containing sialic acid residues—in bryophytes, such as *Physcomitrella patens*.

These and other objects will become apparent from the following description and examples provided herein.

DETAILED DESCRIPTION

The bryophyte cell of the invention is one selected from the group consisting of mosses and liverworts, of species from the genera *Physcomitrella, Funaria, Sphagnum, Ceratodon, Marchantia* and *Sphaerocarpos*. The bryophyte cell is preferably from *Physcomitrella patens*.

The bryophyte cell, such as a *Physcomitrella patens* cell, can be any cell suitable for transformation according to methods of the invention as described herein, and may be a bryophyte protoplast cell, a cell found in protonema tissue or other cell type. Indeed, the skilled addressee will appreciate that bryophyte plant tissue comprising populations of transformed bryophyte cells according to the invention, such as transformed protonema tissue also forms an aspect of the present invention.

According to the present invention there is provided a transformed bryophyte cell, preferably a *Physcomitrella patens* cell, that comprises at least one nucleotide sequence operably linked to an exogenous promoter that drives expression in the said bryophyte cell wherein the said at least one nucleotide sequence encodes a functional mammalian protein that is expressed in the bryophyte cell and is selected from a mammalian UDP-N-acetylglucosamine-2-epimerase/N-acetylmannosamine-6-kinase, a mammalian N-acetylneuraminic acid phosphate synthase (sialic acid synthase), a mammalian CMP-N-acetylneuraminic acid synthase, a mammalian CMP-sialic acid transporter, a galactosyl-transferase, and a mammalian sialyltransferase.

The transformed bryophyte cell may comprise at least one, two, three, four, five, or six of the nucleic acid sequences mentioned hereinabove in relation to the transformed bryophyte cell, such sequences being capable of encoding functional proteins wherein the said nucleic acid sequences are each operably linked to an exogenous promoter. Typically, such nucleotide sequences are mammalian sequences and preferably are selected from human nucleic acid sequences.

The transformed bryophyte cell of the invention typically comprises a beta-1,4 galactosyltransferase, preferably a human beta 1,4 galactosyltransferase nucleotide sequence.

The sialyltransferase used in the transformed bryophyte cells of the invention is typically selected from a mammalian alpha-2,6 or alpha 2,3 sialyltransferase, and is preferably a human alpha-2,6 sialyltransferase nucleotide sequence.

The transformed bryophyte cell of the invention is a cell in which fucosyltransferase and/or xylosyltransferase activity is significantly reduced or eliminated. This effect may e.g. be achieved by using a transformed bryophyte cell of the invention that preferably comprises i) a dysfunctional fucosyltransferase nucleotide sequence and/or ii) a dysfunctional xylosyltransferase nucleotide sequence.

"Dysfunctional" as used herein means that the nominated transferase nucleotide sequences of fucosyltransferase (fucT) and xylosyltransferase (xylT) are substantially incapable of encoding mRNA that codes for functional fucT and xylT proteins that are capable of modifying plant N-linked glycans with plant-like glycoslation patterns comprising 1,3 linked fucosyl and 1,2 linked xylosyl residues. In a preferment, the dysfunctional fucT and xylT plant transferase nucleotide sequences comprise targeted insertions of exogenous nucleotide sequences into endogenous, that is genomic, native fucT and xylT genes comprised in the nuclear bryophyte genome (whether it is a truly native bryophyte genome, that is in bryophyte cells that have not been transformed previously by man with other nucleic acid sequences, or in a transformed nuclear bryophyte genome in which nucleic acid sequence insertions have been made previously of desired nucleic acid sequences) which substantially inhibits or represses the transcription of mRNA coding for functional fucT and xylT transferase activity.

As known by the skilled person bryophyte cells being deficient with respect to fucosyltransferase and/or xylosyltransferase activity can also be produced by other techniques including RNAi and antisense technology. All of these methods lead to a preferred bryophyte cell in which fucosyltransferase and/or xylosyltransferase activity is significantly reduced or eliminated.

Bryophyte cells of the invention or ancestors thereof may be any which have been transformed previously with heterologous genes of interest that code for primary sequences of proteins of interest which are glycosylated with mammalian glycosylation patterns as described herein. Preferably, the glycosylation patterns are of the human type. Alternatively, the bryophyte cell may be transformed severally, that is, simultaneously or over time with nucleotide sequences coding for at least a primary protein sequence of interest, typically at least a pharmaceutical protein of interest for use in humans or mammals such as livestock species including bovine, ovine, equine and porcine species, that require mammalian glycosylation patterns to be placed on them in accordance with the methods of the invention as described herein. Such pharmaceutical glycoproteins for use in mammals, including man include but are not limited to proteins, preferably human proteins, such as VEGF, interferons such as alpha-interferon, beta-interferon, gamma-interferon, blood-clotting factors selected from Factor VII, VIII, IX, X, XI, and XII, fertility hormones including luteinising hormone, follicle stimulating hormone, growth factors including epidermal growth factor, platelet-derived growth factor, granulocyte colony stimulating factor and the like, prolactin, oxytocin, thyroid stimulating hormone, adrenocorticotropic hormone, calcitonin, parathyroid hormone, somatostatin, erythropoietin (EPO), enzymes such as beta-glucocerebrosidase, fusion proteins such as the fusion protein of TNF alpha receptor ligand binding domain with Fc portion of IgG and the like, receptors, surface proteins, transmembrane proteins, and physiologically active fragments thereof. Furthermore, the method of the invention can be used for the production of antibodies such as specific monoclonal antibodies or physiologically active fragments thereof. These antibodies or fragments thereof may be chimeric, humanised or human antibodies.

In a preferment, there is provided a bryophyte cell that comprises i) a nucleotide sequence operably linked to an exogenous promoter that drives expression in the said bryophyte cell wherein said nucleotide sequence encodes a functional mammalian UDP-N-acetylglucosamine-2-epimerase/N-acetylmanno-samine-6-kinase that is expressed in the bryophyte cell, ii) a nucleotide sequence operably linked to an exogenous promoter that drives expression in the said bryophyte cell wherein said nucleotide sequence encodes a functional mammalian N-acetylneuraminic acid phosphate synthase (sialic acid synthase) that is expressed in the bryophyte cell, iii) a nucleotide sequence operably linked to an exogenous promoter that drives expression in the said bryophyte cell wherein said nucleotide sequence encodes a functional mammalian CMP-N-acetylneuraminic acid synthase that is expressed in the bryophyte cell, iv) a nucleotide sequence operably linked to an exogenous promoter that drives expression in the said bryophyte cell wherein said nucleotide sequence encodes a functional mammalian CMP-sialic acid transporter that is expressed in the bryophyte cell, v) a nucleotide sequence operably linked to an exogenous promoter that drives expression in the said bryophyte cell wherein said nucleotide sequence encodes a functional mammalian galactosyl-transferase that is expressed in the bryophyte cell, and vi) a nucleotide sequence operably linked to an exogenous promoter that drives expression in the said bryophyte cell wherein said nucleotide sequence encodes a functional mammalian sialyltransferase that is expressed in the bryophyte cell.

In a preferment, there is provided a transformed bryophyte cell that comprises i) a dysfunctional fucosyltransferase nucleotide sequence, ii) a dysfunctional xylosyltransferase nucleotide sequence, iii) a nucleotide sequence operably linked to an exogenous promoter that drives expression in the said bryophyte cell wherein said nucleotide sequence encodes a functional mammalian UDP-N-acetylglucosamine-2-epimerase/N-acetylmanno-samine-6-kinase that is expressed in the bryophyte cell, iv) a nucleotide sequence operably linked to an exogenous promoter that drives expression in the said bryophyte cell wherein said nucleotide sequence encodes a functional mammalian N-acetylneuraminic acid phosphate synthase (sialic acid synthase) that is expressed in the bryophyte cell, v) a nucleotide sequence operably linked to an exogenous promoter that drives expression in the said bryophyte cell wherein said nucleotide sequence encodes a functional mammalian CMP-N-acetylneuraminic acid synthase that is expressed in the bryophyte cell, vi) a nucleotide sequence operably linked to an exogenous promoter that drives expression in the said bryophyte cell wherein said nucleotide sequence encodes a functional mammalian CMP-sialic acid transporter that is expressed in the bryophyte cell, vii) a nucleotide sequence operably linked to an exogenous promoter that drives expression in the said bryophyte cell wherein said nucleotide sequence encodes a functional galactosyltransferase that is expressed in the bryophyte cell, and viii) a nucleotide sequence operably linked to an exogenous promoter that drives expression in the said bryophyte cell wherein said nucleotide sequence encodes a functional mammalian sialyltransferase that is expressed in the bryophyte cell.

The skilled addressee will appreciate that the enzyme nucleotide sequences may be cDNA sequences or may be genomic DNA sequences and may comprise degeneratively equivalent nucleotide sequences as long as the N-glycan glycosylation pattern on any desired glycosylated exogenous protein produced in the transformed bryophyte cells or bryophyte tissue of the invention is substantially mammalian in pattern—which means comprising sialic acid residues—, if not completely mammalian in pattern, and most preferably, where appropriate, is human in pattern.

Detailed information on the culturing of bryophytes which are suitable for use in the invention, such as *Leptobryum pyriforme* and *Sphagnum magellanicum* in bioreactors, is known in the prior art (see, for example, E. Wilbert, "Biotechnological studies concerning the mass culture of mosses with particular consideration of the arachidonic acid metabolism", Ph.D. thesis, University of Mainz (1991); H. Rudolph and S. Rasmussen, Studies on secondary metabolism of Sphagnum cultivated in bioreactors, Crypt. Bot., 3, 67-73 (1992)). Especially preferred for the purposes of the present invention is the use of *Physcomitrella patens*, since molecular biology techniques are practised on this organism (for a review see R. Reski, Development, genetics and molecular biology of mosses, Bot. Acta, 111, pp. 1-15 (1998)). For cultivation of bryophytes media with (Baur et al. (2005) Plant Biotechnol J 3, 331-340) or without supplements like trace elements can be used (Weise et al. (2006) Appl. Microbiol. Biotechnol., 70, 337-345).

Suitable transformation systems have been developed for the biotechnological exploitation of *Physcomitrella* for the production of heterologous proteins. For example, successful transformations have been carried out by direct DNA transfer into protonema tissue using particle guns. PEG-mediated DNA transfer into moss protoplasts has also been successfully achieved. The PEG-mediated transformation method has been described many times for *Physcomitrella patens* and leads both to transient and to stable transformants (see, for example, K. Reutter and R. Reski, Production of a heterologous protein in bioreactor cultures of fully differentiated moss plants, Pl. Tissue culture and Biotech., 2, 142-147 (1996)). Moreover, marker-free transformation can be achieved by PEG-mediated transformation method with bryophytes as well (Stemmer C, Koch A and Gorr G (2004), Marker-free transformation of *Physcomitrella patens*, Moss 2004, The 7$^{th}$ Annual Moss International Conference, Freiburg, Germany) and can be used for subsequent introduction of multiple nucleotide sequences.

In a further aspect of the invention there is provided a method of producing at least an exogenous glycosylated mammalian protein in a bryophyte cell that comprises:

i) introducing into the said bryophyte cell at least one isolated nucleic acid sequence that comprises a nucleic acid sequence operably linked to an exogenous promoter that drives expression in a bryophyte cell wherein the said at least one isolated nucleic acid sequence encodes a functional protein, preferably a human protein, that is expressed in the bryophyte cell and is selected from a mammalian UDP-N-acetylglucosamine-2-epimerase/N-acetylmannosamine-6-kinase, a mammalian N-acetyl-neuraminic acid phosphate synthase (sialic acid synthase), a mammalian CMP-N-acetylneuraminic acid synthase, a mammalian CMP-sialic acid transporter, a galactosyltransferase, and a mammalian sialyltransferase; and ii) introducing into said cell a further isolated nucleic acid sequence that comprises a nucleic acid sequence operably linked to an exogenous promoter that drives expression in a bryophyte cell wherein said nucleic acid encodes at least one glycosylated mammalian polypeptide.

If step ii) has already been accomplished the method comprises:

i) using a transformed bryophyte cell that comprises a nucleic acid sequence operably linked to an exogenous promoter that drives expression in said bryophyte cell wherein said nucleic acid encodes at least one glycosylated mammalian polypeptide; and ii) introducing into the said bryophyte cell at least one isolated nucleic acid sequence that comprises a nucleic acid sequence operably linked to an exogenous promoter that drives expression in a bryophyte cell wherein the said at least one isolated nucleic acid sequence encodes a functional protein that is expressed in the bryophyte cell and is selected from a mammalian UDP-N-acetylglucosamine-2-epimerase/N-acetylmanno-samine-6-kinase, a mammalian N-acetylneuraminic acid phosphate synthase (sialic acid synthase), a mammalian CMP-N-acetylneu-raminic acid synthase, a mammalian CMP-sialic acid transporter, a galactosyltransferase, and a mammalian sialyltransferase.

The method of transforming the bryophyte cell may comprise transforming the said cell with at least one, two, three, four, five, or six of the nucleic acid sequences mentioned hereinabove in relation to the transformed bryophyte cell, such sequences being capable of encoding functional proteins wherein the said nucleic acid sequences are each operably linked to an exogenous promoter. Typically, such nucleotide sequences are mammalian sequences and preferably are selected from human nucleic acid sequences.

The method of the invention typically comprises introducing a functional galactosyltransferase, for example a mammalian beta-1,4 galactosyltransferase, preferably a human beta 1,4 galactosyltransferase nucleotide sequence into the transformed bryophyte cell of the invention.

The method of the invention typically also employs a sialyltransferase used in the transformed bryophyte cells of the invention which is typically encoded by a polynucleotide selected from a mammalian alpha-2,6 or alpha 2,3 sialyltransferase nucleotide sequence, and is preferably a human alpha-2,6 sialyltransferase nucleotide sequence.

The transformed bryophyte cell of the invention is typically a cell in which fucosyltransferase and/or xylosyltransferase activity is significantly reduced or eliminated.

In a preferred embodiment of the present invention there is provided a method of producing at least a heterologous or exogenous glycosylated mammalian protein in a transformed bryophyte cell that comprises:

i) introducing into said cell a first isolated nucleic acid sequence that comprises nucleic acid operably linked to an exogenous promoter that drives expression in a bryophyte cell wherein said nucleic acid encodes at least one UDP-N-acetylglucosamine-2-epimerase/N-acetylmannosamine-6-kinase;

ii) introducing into said cell a further isolated nucleic acid sequence that comprises nucleic acid operably linked to an exogenous promoter that drives expression in a bryophyte cell wherein said nucleic acid encodes at least one N-acetylneuraminic acid phosphate synthase (sialic acid synthase);

iii) introducing into said cell a further isolated nucleic acid sequence that comprises nucleic acid operably linked to an exogenous promoter that drives expression in a bryophyte cell wherein said nucleic acid encodes at least one CMP-N-acetylneuraminic acid synthase;

iv) introducing into said cell a further isolated nucleic acid sequence that comprises nucleic acid operably linked to an exogenous promoter that drives expression in a bryophyte cell wherein said nucleic acid encodes at least one mammalian CMP-sialic acid transporter polypeptide;

v) introducing into said cell a further isolated nucleic acid sequence that comprises nucleic acid operably linked to an exogenous promoter that drives expression in a bryophyte cell wherein said nucleic acid encodes at least one galactosyltransferase polypeptide;

vi) introducing into said cell a further isolated nucleic acid sequence that comprises nucleic acid operably linked to an exogenous promoter that drives expression in a bryophyte cell wherein said nucleic acid encodes at least one mammalian sialyltransferase polypeptide;

vii) introducing into said cell a further isolated nucleic acid sequence that comprises nucleic acid operably linked to an exogenous promoter that drives expression in a bryophyte cell wherein said nucleic acid encodes at least one glycosylated mammalian polypeptide.

As alluded to herein, the at least one galactosyltransferase polypeptide is preferably a mammalian beta-1,4 galactosyltransferase (beta-1,4 galT) and most preferably is a human beta-1,4 galactosyltransferase polypeptide, and the at least one mammalian sialyltransferase polypeptide is preferably an alpha-2,3 or alpha-2,6 sialyltransferase and most preferably is a human alpha-2,6 sialyltransferase polypeptide.

In a further preferment the above method additionally comprises the following steps:

viii) a nucleotide sequence that renders the endogenic fucosyltransferase nucleotide sequence dysfunctional;

ix) a nucleotide sequence that renders the endogenic xylosyltransferase nucleotide sequence dysfunctional.

Alternatively, the above method makes use of a bryophyte cell in which fucosyltransferase and/or xylosyltransferase activity is significantly reduced or eliminated.

Preferably all glycosylated mammalian proteins mentioned hereinabove are of the human type. Other proteins that are contemplated for production in the present invention include proteins for use in veterinary care and may correspond to animal homologues of the human proteins mentioned herein.

An exogenous promoter is one that denotes a promoter that is introduced in front of a nucleic acid sequence of interest and is operably associated therewith. Thus an exogenous promoter is one that has been placed in front of a selected nucleic acid component as herein defined and does not consist of the natural or native promoter usually associated with the nucleic acid component of interest as found in wild type circumstances. Thus a promoter may be native to a bryophyte cell of interest but may not be operably associated with the nucleic acid of interest in front in wild-type bryophyte cells. Typically, an exogenous promoter is one that is transferred to a host bryophyte cell from a source other than the host cell.

The cDNA's encoding the (mammalian) enzymes and the glycosylated mammalian proteins as described herein contain at least one type of promoter that is operable in a bryophyte cell, for example, an inducible or a constitutive promoter operatively linked to a (mammalian) enzyme encoding nucleic acid sequence and/or second nucleic acid sequence for a glycosylated mammalian protein as herein defined and as provided by the present invention. As discussed, this enables control of expression of the genes.

The term "inducible" as applied to a promoter is well understood by those skilled in the art. In essence, expression under the control of an inducible promoter is "switched on" or increased in response to an applied stimulus (which may be generated within a cell or provided exogenously). The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus. The preferable situation is where the level of expression increases upon application of the relevant stimulus by an amount effective to alter a phenotypic characteristic. Thus an inducible (or "switchable") promoter may be used which causes a basic level of expression in the absence of the stimulus which level is too low to bring about a desired phenotype (and may in fact be zero). Upon application of the stimulus, expression is increased (or switched on) to a level, which brings about the desired phenotype.

As alluded to herein, bryophyte expression systems are also known to the man skilled in the art. A bryophyte promoter, in particular a *Physcomitrella patens* promoter, is any DNA sequence capable of binding a host DNA-dependent RNA polymerase and initiating the downstream (3') transcription of a coding sequence (e.g. structural gene) into mRNA. A promoter will have a transcription initiation region which is usually placed proximal to the 5' end of the coding sequence. This transcription initiation region usually includes an RNA polymerase binding site (the "TATA Box") and a transcription initiation site. A bryophyte promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

The skilled addressee will appreciate that bryophyte promoter sequences encoding enzymes in bryophyte metabolic pathways can provide particularly useful promoter sequences.

In addition, synthetic promoters which do not occur in nature may also function as bryophyte promoters. For example, UAS sequences of one byrophyte promoter may be joined with the transcription activation region of another bryophyte promoter, creating a synthetic hybrid promoter. An example of a suitable promoter is the one used in the TOP 10 expression system for *Physcomitrella patens* by Zeidler et al. (1996) Plant. Mol. Biol. 30, 199-205). Furthermore, a bryophyte promoter can include naturally occurring promoters of non-bryophyte origin that have the ability to bind a bryophyte DNA-dependent RNA polymerase and initiate transcription. Examples of such promoters include those described, inter alia, the rice P-Actin 1 promoter and the *Chlamydomonas* RbcS promoter (Zeidler et al. (1999) J. Plant Physiol. 154, 641-650), Cohen et al., Proc. Natl. Acad. Sci. USA, 77: 1078, 1980; Henikoff et al., Nature, 283: 835, 1981; Hollenberg et al., Curr. Topics Microbiol. Immunol., 96: 119, 198 1; Hollenberg et al., "The Expression of Bacterial Antibiotic Resistance Genes in the Yeast *Saccharomyces cerevisiae*", in: Plasmids of Medical, Environmental and Commercial Importance (eds. K. N. Timms and A. Puhler), 1979; Mercerau-Puigalon et al., Gene, 1 1: 163, 1980; Panthier et al., Curr. Genet., 2: 109, 1980.

A DNA molecule may be expressed intracellularly in bryophytes. A promoter sequence may be directly linked with the DNA molecule, in which case the first amino acid at the N-terminus of the recombinant protein will always be a methionine, which is encoded by the AUG start codon on the mRNA. If desired, methionine at the N-terminus may be cleaved from the protein by in vitro incubation with cyanogen bromide.

Alternatively, foreign proteins can also be secreted from the bryophyte cell into the growth media by creating chimeric DNA molecules that encode a fusion protein comprised of a leader sequence fragment that provides for secretion in or out of bryophyte cells of the foreign protein. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell.

DNA encoding suitable signal sequences can be derived from genes for bryophyte proteins which are targeted to the secretory pathway, such as leaders of non-bryophyte origin, such as a VEGF leader, exist that may also provide for secretion in bryophyte cells.

Transcription termination sequences that are recognized by and functional in bryophyte cells are regulatory regions located 3' to the translation stop codon, and thus together with the promoter flank the coding sequence. These sequences direct the transcription of an mRNA which can be translated into the polypeptide encoded by the DNA. An example of a suitable termination sequence that works in *Physcomitrella patens* is the termination region of Cauliflower mosaic virus.

Typically, the components, comprising a promoter, leader (if desired), coding sequence of interest, and transcription termination sequence, are put together into expression constructs of the invention. Expression constructs are often maintained in a DNA plasmid, which is an extrachromosomal element capable of stable maintenance in a host, such as a bacterium. The DNA plasmid may have two origins of replication, thus allowing it to be maintained, for example, in a bryophyte for expression and in a prokaryotic host for cloning and amplification. Generally speaking it is sufficient if the plasmid has one origin of replication for cloning and amplification in a prokaryotic host cell. In addition, a DNA plasmid may be either a high or low copy number plasmid. A high copy number plasmid will generally have a copy number ranging from about 5 to about 200, and usually about 10 to about 150. A host containing a high copy number plasmid will preferably have at least about 10, and more preferably at least about 20. Either a high or low copy number vector may be selected, depending upon the effect of the vector and the foreign protein on the host (see, e.g., Brake et al., supra).

Alternatively, the expression constructs can be integrated into the bryophyte genome with an integrating vector. Integrating vectors usually contain at least one sequence homologous to a bryophyte chromosome that allows the vector to integrate, and preferably contain two homologous sequences flanking the expression construct. An integrating vector may be directed to a specific locus in moss by selecting the appropriate homologous sequence for inclusion in the vector as described and exemplified herein. One or more expression constructs may integrate. The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Usually, extrachromosomal and integrating expression constructs may contain selectable markers to allow for the selection of bryophyte cells that have been transformed. In addition marker-free transformation methods can be used.

Selectable markers may include biosynthetic genes that can be expressed in the moss host, such as the G418 or hygromycin B resistance genes, which confer resistance in bryophyte cells to G418 and hygromycin B, respectively. In addition, a suitable selectable marker may also provide bryophyte cells with the ability to grow in the presence of toxic compounds, such as metal.

Alternatively, some of the above-described components can be put together into transformation vectors. Transformation vectors are usually comprised of a selectable marker that is either maintained in a DNA plasmid or developed into an integrating vector, as described above.

Methods of introducing exogenous DNA into bryophyte cells are well-known in the art, and are described inter alia by Schaefer D. G. "Principles and protocols for the moss *Physcomitrella patens*", (May 2001) Institute of Ecology, Laboratory of Plant Cell Genetics, University of Lausanne Didier.Schaefer@ie-pc.unil.ch; Reutter K. and Reski R., Plant Tissue Culture and Biotechnology September 1996, Vol. 2, No. 3; Zeidler M et al., (1996), Plant Molecular Biology 30:199-205.

Those skilled in the art are well able to construct vectors and design protocols for recombinant nucleic acid sequence or gene expression as described above. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Second Edition, Ausubel et al. eds., John Wiley & Sons, 1992. The disclosures of Sambrook et al. and Ausubel et al. are incorporated herein by reference.

Naturally, the skilled addressee will appreciate that each nucleic acid sequence coding for the appropriate (human) enzymes and polypeptides to be glycosylated, and including those to be sialylated, will be under regulatory control of its own exogenous promoter and terminator. When two or more target proteins are destined to be produced from a single carrier RNA it is preferable if they are able to be readily separated, for example by binding to different protein-specific antibodies (monoclonal or polyclonal) in the harvesting phase of the bryophyte cell culture system.

As described above, selectable genetic markers may facilitate the selection of transgenic bryophyte cells and these may consist of chimeric genes that confer selectable phenotypes as alluded to herein.

When introducing selected human enzyme nucleic acid sequences and polypeptide sequences for glycosylation and/or sialylation into a bryophyte cell, certain considerations must be taken into account, well known to those skilled in the art. The nucleic acid(s) to be inserted should be assembled within a construct, which contains effective regulatory elements, which will drive transcription. There must be available a method of transporting the construct into the cell. Once the construct is within the cell membrane, integration into the endogenous chromosomal material either will or will not occur.

The present invention provides a nucleic acid vector suitable for transformation of a bryophyte cell and including at least one isolated polynucleotide sequence encoding at least one functional polypeptide selected from a mammalian UDP-N-acetylglucosamine-2-epimerase/N-acetylmannosamine-6-kinase, a mammalian N-acetyl-neuraminic acid phosphate synthase (sialic acid synthase), a mammalian CMP-N-acetyl-neuraminic acid synthase, a mammalian CMP-sialic acid transporter, a galactosyltransferase, and a mammalian sialyl-transferase. The artisan will appreciate that the invention also provides a set of nucleic acid vectors suitable for transformation of a bryophyte cell wherein said set comprises at least two vectors each including at least one isolated polynucleotide sequence as defined hereinbefore. Likewise, the invention provides this set of nucleic acid vectors for use in a method of producing a transformed bryophyte cell as defined hereinbefore.

The invention further encompasses a host cell transformed with vectors or constructs as set forth above, especially a non-animal eukaryotic cell, such as a bryophyte, yeast, ciliate or algae cell, or a prokaryote (microbial) cell. Thus, a host cell, such as a bryophyte cell, including nucleotide sequences of the invention as herein indicated is provided. Within the cell, the nucleotide sequence may be incorporated within the chromosome.

Also according to the invention there is provided a bryophyte cell having incorporated into its genome at least a nucleotide sequence, particularly heterologous nucleotide sequences, as provided by the present invention under operative control of regulatory sequences for control of expression as herein described. The coding sequence may be operably linked to one or more regulatory sequences which may be heterologous or foreign to the nucleic acid sequences employed in the invention, such as not naturally associated with the nucleic acid sequence(s) for its (their) expression. The nucleotide sequence according to the invention may be placed under the control of an externally inducible promoter to place expression under the control of the user. A further aspect of the present invention provides a method of making such a bryophyte cell, particularly a *Physcomitrella patens* cell involving introduction of nucleic acid sequence(s) contemplated for use in the invention or at least a suitable vector or set of vectors including the sequence(s) contemplated for use in the invention into a bryophyte cell and causing or allowing recombination between the vector(s) and the bryophyte cell genome to introduce the said sequences into the genome. The invention extends to bryophyte cells, particularly *Physcomitrella patens* cells containing a Ga1T nucleotide and/or a nucleotide sequence coding for a polypeptide sequence destined for the addition of a mammalian glycosylation pattern thereto and suitable for use in the present invention as a result of introduction of the nucleotide sequence into an ancestor cell.

The term "heterologous" may be used to indicate that the gene/sequence of nucleotides in question have been introduced into bryophyte cells or an ancestor thereof, using genetic engineering, i.e. by human intervention. A transgenic bryophyte cell, i.e. transgenic for the nucleotide sequence(s) in question, may be provided. The transgene may be on an extra-genomic vector or incorporated, preferably stably, into the genome. A heterologous gene may replace an endogenous equivalent gene, ie one that normally performs the same or a similar function, or the inserted sequence may be additional to the endogenous gene or other sequence. An advantage of introduction of a heterologous gene is the ability to place expression of a sequence under the control of a promoter of choice, in order to be able to influence expression according to preference. Nucleotide sequences heterologous, or exogenous or foreign, to a bryophyte cell may be non-naturally occurring in cells of that type, strain or species. Thus, a nucleotide sequence may include a coding sequence of or derived from a particular type of bryophyte cell, such as a *Physcomitrella patens* cell, placed within the context of a bryophyte cell of a different type or species. A further possibility is for a nucleotide sequence to be placed within a bryophyte cell in which it or a homologue is found naturally, but wherein the nucleotide sequence is linked and/or adjacent to nucleic acid which does not occur naturally within the cell, or cells of that type or species or strain, such as operably linked to one or more regulatory sequences, such as a promoter sequence, for control of expression. A sequence within a bryophyte or other host cell may be identifiably heterologous, exogenous or foreign.

The present invention also encompasses the desired polypeptide expression product of the combination of nucleic acid molecules according to the invention as disclosed herein or obtainable in accordance with the information and suggestions herein. Also provided are methods of making such an expression product by expression from nucleotide sequences encoding therefore under suitable conditions in suitable host cells e.g. *E. coli*. Those skilled in the art are well able to construct vectors and design protocols and systems for expression and recovery of products of recombinant gene expression.

The present invention also contemplates the use of at least one polynucleotide sequence encoding at least one protein selected from a mammalian UDP-N-acetyl-glucosamine-2-epimerase/N-acetylmannosamine-6-kinase, a mammalian N-acetylneuraminic acid phosphate synthase (sialic acid synthase), a mammalian CMP-N-acetylneuraminic acid synthase, a mammalian CMP-sialic acid transporter, a galactosyltransferase, and a mammalian sialyl-transferase in the production of a transgenic non-animal cell, wherein said transgenic non-animal cell preferably is a bryophyte, yeast, ciliate or algae cell.

In a further preferment the host cell of the invention is comprised in a bryophyte, or a bryophyte part, or an extract or derivative of a bryophyte or in a bryophyte cell culture.

Furthermore, there is provided a bryophyte plant or bryophyte tissue comprising a bryophyte cell as defined hereinbefore.

The present invention also provides a method of producing a transformed bryophyte plant, the method including incorporating at least one nucleic acid vector or a set of nucleic acid vectors as defined hereinbefore into a bryophyte cell and regenerating a bryophyte from said cell.

Moreover, the present invention provides a method of producing sialic acid or CMP-sialic acid in a transformed non-mammalian eucaryotic cell, tissue or organism, that comprises i) transforming said non-mammalian eucaryotic cell, tissue or organism with at least one polynucleotide sequence encoding at least one polypeptide selected from a mammalian UDP-N-acetyl-glucosamine-2-epimerase N-acetylmannosamine-6-kinase, a mammalian N-acetylneuraminic acid phosphate synthase (sialic acid synthase), a mammalian CMP-N-acetylneuraminic acid synthase;

ii) introducing at least one vector or a set of vectors as defined in any one of claims 23 to 25 into said non-mammalian eucaryotic cell, tissue or organism; or iii) using an already transformed non-mammalian eucaryotic cell, tissue or organism that comprises at least one polynucleotide sequence encoding at least one polypeptide selected from a mammalian UDP-N-acetyl-glucosamine-2-epimerase/N-acetyl-mannosamine-6-kinase, a mammalian N-acetylneuraminic acid phosphate synthase (sialic acid synthase), a mammalian CMP-N-acetylneuraminic acid synthase;

and, optionally, recovering, purifying or isolating the sialic acid or CMP-sialic acid from the cell, tissue or organism as treated or defined in i), ii) and/or iii).

In a preferment said non-mammalian cell, tissue or organism is a yeast, ciliate or algae cell, tissue or organism.

A polypeptide produced according to the present invention may be an allele, variant, fragment, derivative, mutant or homologue of the (a) polypeptides as mentioned herein. The allele, variant, fragment, derivative, mutant or homologue may have substantially the same function of the polypeptides alluded to above and as shown herein or may be a functional mutant thereof. In the context of pharmaceutical proteins as described herein for use in humans, the skilled addressee will appreciate that the primary sequence of such proteins and their glycosylation pattern will mimick or preferably be identical to that found in humans.

"Homology" in relation to an amino acid sequence of the invention may be used to refer to identity or similarity, preferably identity. As noted already above, high level of amino acid identity may be limited to functionally significant domains or regions, e.g. any of the domains identified herein.

In particular, homologues of the particular bryophyte-derived polypeptide sequences provided herein, are provided by the present invention, as are mutants, variants, fragments and derivatives of such homologues. Such homologues are readily obtainable by use of the disclosures made herein. Naturally, the skilled addressee will appreciate that homologues of the glycosylated protein sequences per se, other than those homologues that due to the degeneracy of the genetic code give rise to amino acid sequences that are true copies (i.e. 100% identical) of the mammalian proteins of interest, and especially of human proteins of interest, are encompassed within the present invention. Thus the present invention also extends to polypeptides which include amino acid sequences with human enzymes function as defined herein and as obtainable using sequence information as provided herein. The homologues may at the amino acid level have homology, that is identity, with the amino acid sequences described in the prior art as described herein i.e. under the database accession numbers provided in the examples section, preferably at least about 50%, or at least 55%, or at least about 60%, or at least about 65%, or at least about 70%, or at least about 75%, or at least about 80% homology, or at least about 85%, or at least about 88% homology, or at least about 90% homology and most preferably at least about 95% or greater homology provided that such proteins have activity that fits within the context of the present invention.

In certain embodiments, an allele, variant, derivative, mutant derivative, mutant or homologue of the specific sequence may show little overall homology, say about 20%, or about 25%, or about 30%, or about 35%, or about 40% or about 45%, with the specific sequence. However, in functionally significant domains or regions, the amino acid homology may be much higher. Putative functionally significant domains or regions can be identified using processes of bioinformatics, including comparison of the sequences of homologues.

Functionally significant domains or regions of different polypeptides may be combined for expression from encoding nucleic acid as a fusion protein. For example, particularly advantageous or desirable properties of different homologues may be combined in a hybrid protein, such that the resultant expression products, with enzyme activity, may include fragments of various parent proteins, if appropriate.

Similarity of amino acid sequences may be as defined and determined by the TBLASTN program, of Altschul et al. (1990) *J. Mol. Biol.* 215: 403-10, which is in standard use in the art. In particular, TBLASTN 2.0 may be used with Matrix BLOSUM62 and GAP penalties: existence: 11, extension: 1. Another standard program that may be used is BestFit, which is part of the Wisconsin Package, Version 8, September 1994, (Genetics Computer Group, 575 Science Drive, Madison, Wis., USA, Wisconsin 53711). BestFit makes an optimal alignment of the best segment of similarity between two sequences. Optimal alignments are found by inserting gaps to maximize the number of matches using the local homology algorithm of Smith and Waterman (*Adv. Appl. Math.* (1981) 2: 482-489). Other algorithms include GAP, which uses the Needleman and Wunsch algorithm to align two complete sequences that maximizes the number of matches and minimizes the number of gaps. As with any algorithm, generally the default parameters are used, which for GAP are a gap creation penalty=12 and gap extension penalty=4. Alternatively, a gap creation penalty of 3 and gap extension penalty of 0.1 may be used. The algorithm FASTA (which uses the method of Pearson and Lipman (1988) *PNAS USA* 85: 2444-2448) is a further alternative.

Use of either of the terms "homology" and "homologous" herein does not imply any necessary evolutionary relationship between compared sequences, in keeping for example with standard use of terms such as "homologous recombination" which merely requires that two nucleotide sequences are sufficiently similar to recombine under the appropriate conditions.

It is to be understood that the teaching of all references cited herein is incorporated into the teaching of the specification.

EXAMPLES

Methods and Materials

Plant Material

The wild-type strain of *Physcomitrella patens* (Hedw.) B.S.G. characterised by Reski et al. ((1994) Genome analysis of the moss *Physcomitrella patens* (Hedw.) B.S.G. *Mol Gen Genet* 244, 352-359)) was used. It is a subculture of strain 16/14 which was collected by H. L. K. Whitehouse in Gransden Wood, Huntingdonshire, UK and was propagated by Engel ((1968) *Am J Bot* 55, 438-446)). Glyco-engineered transgenic *Physcomitrella* strains lacking the two plant-specific sugar residues on the core structure of N-glycans (Koprivova et al. (2004) Plant Biotechnol J 2, 517-523) and/or containing human 1,4 galactosyltransferase (Huether et al. (2005) Plant Biol 7, 292-299) were used also.

Standard Culture Conditions

Plants were grown axenically under sterile conditions in plain inorganic liquid modified Knop medium (1000 mg/l $Ca(NO_3)_2 \times 4H_2O$ 250 mg/l KCl, 250 mg/l $KH_2PO_4$, 250 mg/l $MgSO_4 \times 7 H_2O$ and 12.5 mg/l $FeSO_4 \times 7 H_2O$; pH 5.8 (Reski and Abel (1985) *Planta* 165, 354-358). Culture conditions can be varied e.g. as described by Baur et al. (2005) Plant Biotechnol J 3, 331-340 or Weise et al. (2006) Appl Microbiol Biotechnol, 70, 337-345). Plants were grown in 500 ml Erlenmeyer flasks containing 200 ml of culture medium and flasks were shaken on a Certomat R shaker (B. Braun Biotech International, Germany) set at 120 rpm. Conditions in the growth chamber were 25+/−3° C. and a light-dark regime of 16:8 h. The flasks were illuminated from above by two fluorescent tubes (Osram L 58 W/25) providing 35 micromols$^{-1}$m$^{-2}$. The cultures were subcultured once a week by disintegration using an Ultra-Turrax homogenizer (IKA, Staufen, Germany) and inoculation of two new 500 ml Erlenmeyer flasks containing 100 ml fresh Knop medium.

Protoplast Isolation and Transformation

Protoplast isolation was performed as described previously (Baur et al. (2005) J Biotechnol, 119, 332-342). For counting protoplasts a small volume of the suspension was transferred to a Fuchs-Rosenthal-chamber. Transformation was performed by PEG-mediated direct DNA transfer into protoplasts with selection markers (Strepp et al. (1998) *Proc Natl Acad Sci* USA 95, 4368-4373) or markerfree (Stemmer C, Koch A and Gorr G (2004) Marker-free transformation of *Physcomitrella patens*. Moss 2004, The 7$^{th}$ Annual Moss International Conference, Freiburg, Germany). Co-transformations were performed by introducing the relevant DNA constructs simultaneously into the protoplasts by PEG-mediated DNA transfer.

PCR-Screening

Introduction of the heterologous DNA constructs was analysed by PCR using the appropriate primers (see below).

Analysis of Sialic Acids (Neu5Ac)

For isolation of glycoproteins tissue was suspended in 15 ml of 25 mM Tris/HCl buffer of pH 7.5—containing 2 mM dithiothreitol and 1 µg/ml leupeptin—and homogenised with an ultraturrax. Triton X-100 (0.25%, w/v) was added to the slurry, and the mixture stirred for 60 min at 4° C. The suspension was centrifuged and the soluble material passed through a 0.45 µm filter. The extracts were dialysed extensively against 25 mM ammonium acetate of pH 6.0. The resulting dialysate was mixed with an equal volume of 4 M acetic acid and kept for 3 h at 80° C. The samples were then ultrafiltrated using a 3 kDa cutoff Centriprep YM-3 device (Amicon). The filtrate was concentrated in vacuo.

50 µl aliquots were derivatized with DMB (Altmann and Lomonossoff (2000), J. Gen. Virol. 81, 1111-1114; Hara et al. (1987), Anal. Biochem. 164, 138-145). DMB-labelled keto sugar acids were separated on a reversed phase column (Thermo Hypersil ODS, 250×4 mm, 5 µm) eluted with 50 mM ammonium acetate, pH 5.5, at a flow rate of 1.2 ml/min. Analytes were eluted with a shallow gradient from 7.6 to 11.4% acetonitrile in 20 min and detected fluorimetrically (Hara et al. (1987), Anal. Biochem. 164, 138-145).

Isolated fractions containing DMB-Neu5Ac were analysed by ESI mass spectrometric (ESI-MS) analysis. Activated sialic acid (CMP-Neu5Ac) was analysed by ESI-MS in the MSMS modus.

EXAMPLES

1.1 Cloning of Human UDP-N-acetylglucosamine-2-epimerase/N-acetylmannosamine-6-kinase cDNA encoding human UDP-N-acetylglucosamine-2-epimerase/N-acetylmannosamine-6-kinase (accession number: AF155663) was cloned into the plant expression vector pRT101 (Toepfer et al. (1987) Nucl Acids Res 15, 5890). In the resulting construct UDP-N-acetylglucosamine-2-epimerase/N-acetylmannosamine-6-kinase was under regulation of the 35S promoter and 35S terminator—together termed as expression construct. For the transformation procedure the expression construct was excised. The linearised fragment containing UDP-N-acetylglucosamine-2-epimerase/N-acetylmannosamine-6-kinase under regulation of the 35S promoter and 35S terminator was used for transformation of *Physcomitrella patens* strains.

In a parallel approach the cDNA encoding human UDP-N-acetylglucosamine-2-epimerase/N-acetylmannosamine-6-kinase (accession number: AF155663) was cloned into the plasmid pBS under regulation of the tub3 promoter (accession number: AY724471) and the terminator of the alpha 1,3 fucosyltransferase gene of *Physcomitrella patens* (Pp). In advance to cloning the human UDP-N-acetylglucosamine-2-epimerase/N-acetylmannosamine-6-kinase cDNA into pBS the terminator of the alpha 1,3 fucosyltransferase gene (5'-CGGTGATCCCGTTTTCATATCAGTGTAT-TATCATCAGTGACTGCATATTGACACCCAATTCTGA TGATTTTTTATTTTTTATTTTT-TATTTTTTTTGGTATGGTTACAT-GCTTTTCAGAGGTTTCTAT GCCGCTGAGTATTTTC-CTGAATCGCGAGGTGTGACAGGTTATCTGCGCCGT CCACCCAATATTT TATGATGAGTCGATGATTCGT-GAGACTAATCTAGCTTAACCTTTTTCT-TACTGGCAAGTCAAAA TTGAGTT-TAAAATATTTCAGTATCCTGTTAGTAATTTCAGACA CATGTATTCTATGTCTCATAC TCTTTACGTGAAAGT-TCAACTGACT-TATATTTTGTCGTTTTTCTGTAGAT-CACTGTTTTAGCGC ATACAAAGACAATTGTCTAAATATTTT-TAAAGAAGGTGATATTTTATTATAA-GATAGAAGTCAA TATGTTTTTTTGTTATGCACAT-GACTTGAATAAAATAAATTTTTTTGTTAGATTTAAA TACTTT TTGAATTATAGCTTTGTTGAAATTAAG-GAATTTATATTCATAAGAAGCTACTCGAACAAATTTA CAAAGAGAACATTTGATAAGTAAAAG-TAATTAAAAGTTTTTTTTAATTTAAAAA-GATTAATTTT TATTAATAAGAAGAACTTGGAAAGT-TAGAAAAATATTTAACTTTAAAAATTAAGAAAACA AGGC AAAACTTTAATTTACAAATACTTAATG-TAGATTAATTTTCTTATTATATATTAGCACAAATTAT CATTATGTGATATTTTATGTTATTGT-3') (SEQ ID NO 1) of *Physcomitrella patens* was amplified by PCR using primer MoB558 (5'-GTTCCGCGGTGATCCCGTTTTCATAT-CAGTGTATT-3') (SEQ ID NO 2) and primer MoB557 (5'-TTTGAGCTCTACGTAACAATAACAT-AAAATAT-CACA-3') (SEQ ID NO 3). The amplified fragment was cut with SacII and SacI and was ligated into pBS which was cut also with SacII and SacI.

cDNA encoding human UDP-N-acetylglucosamine-2-epimerase/N-acetylmannosamine-6-kinase (accession number: AF155663) was ligated with the Pp tub3 promoter and 5'UTR (accession number: AY724471) and amplified by overlapping PCR using the primers MOB1108 (5'-GATGGATCCAT-TGCCAATGTATTGATTGGC-3') (SEQ ID NO 4); MOB1124 (5'-GTTATTTCCATTCTTCTCCATCT-TCGCTAAGGATGATCTAC-3') (SEQ ID NO 5) and MOB1125 (5'-GTCTCTAGACTAGTAGATCCTGCGTGT-3') (SEQ ID NO 6). The resulting fragment was cut with BamHI and XbaI and was ligated into pBS containing the terminator of the Pp alpha 1,3 fucosyltransferase gene and cut with BamHI and XbaI. For transformation of *Physcomitrella patens* the KpnI and SnaBI excised expression construct comprising Pp tub3 promoter, cDNA of human UDP-N-acetylglucosamine-2-epimerase/N-acetylmanno-samine-6-kinase and the terminator of the Pp alpha 1,3 fucosyltransferase gene was used.

1.2 Cloning of Human N-acetylneuraminic acid phosphate synthase cDNA encoding human N-acetylneuraminic acid phosphate synthase (accession number: NM_018946) was cloned into the plant expression vector pRT101 (Toepfer et al. (1987) Nucl Acids Res 15, 5890). The cDNA encoding human N-acetylneuraminic acid phosphate synthase was amplified by PCR using primer_MOB785 (5'-GGCCTGCAGATGC-CGCTGGAGCTGGAGCTG-3') (SEQ ID NO 7) and primer MOB786 (5'-GCCGGATCCTTAAGACT-TGATTTTTTTGCCATGA-3') (SEQ ID NO 8). The amplification product was cut with PstI and BamHI and cloned into pRT101. In the resulting construct N-acetylneuraminic acid phosphate synthase was under regulation of the 35S promoter and 35S terminator—together termed as expression construct. For transformation procedure the expression construct was excised with Sph I. The linearised fragment containing N-acetylneuraminic acid phosphate synthase under regulation of the 35S promoter and 35S terminator was used for transformation of *Physcomitrella patens* strains.

1.3 Cloning of Human CMP-N-acetylneuraminic acid synthase cDNA encoding human CMP-N-acetylneuraminic acid synthase (accession number: NM_018686) was cloned into the plant expression vector pRT101 (Toepfer et al. (1987) Nucl Acids Res 15, 5890). The cDNA coding for human CMP-N-acetylneuraminic acid synthase was amplified by PCR using primer MOB835 (5'-ATCGAATTCATG-GACTCGGTGGAGAAGGG-31) (SEQ ID NO 9) and primer MOB836 (5'-TGAGGATCCCTATTTTTGGCAT-GAATTATTAACCT-3') (SEQ NO ID 10). The amplification product was cut with EcoRI and BamHI and cloned into pRT101. In the resulting construct CMP-N-acetylneuraminic acid synthase was under regulation of the 35S promoter and 35S terminator—together termed as expression construct. For transformation procedure the expression construct was excised with Sph I. The linearised fragment containing CMP-N-acetylneuraminic acid synthase under regulation of the 35S promoter and 35S terminator was used for transformation of *Physcomitrella patens* strains.

1.4 Cloning of Human CMP-sialic Acid Transporter cDNA encoding human CMP-sialic acid transporter (accession number: NM_006416) was cloned into the plant expression vector pRT101 (Toepfer et al. (1987) Nucl Acids Res 15, 5890). The cDNA coding for human CMP-sialic acid transporter was amplified by PCR using primer MOB638 (5'-GTCGAGCTCGGA-ACCATGGCTGCCCCGA-3')

(SEQ ID NO 11) and primer MOB639 (5'-ATCGGATCCT-CACACACCAATAACTCTC-3') (SEQ ID NO 12). The resulting fragment was cut with SacI and BamHI and cloned into pRT101. In the resulting construct CMP-sialic acid transporter was under regulation of the 35S promoter and 35S terminator—together termed as expression construct. For transformation procedure the expression construct was excised with Hind III. The linearised fragment containing CMP-sialic acid transporter under regulation of the 35S promoter and 35S terminator was used for transformation of *Physcomitrella patens* strains.

1.5 Cloning of Human beta-1,4 galactosyltransferase

Cloning of human beta-1,4 galactosyltransferase was performed as described by Huether et al. ((2005) Plant Biol 7, 292-299). In the resulting construct beta-1,4 galactosyltransferase was under regulation of the 35S promoter and 35S terminator—together termed as expression construct. For transformation procedure the expression construct was excised. The linearised fragment containing beta-1,4 galactosyltransferase under regulation of the 35S promoter and 35S terminator was used for transformation of *Physcomitrella patens* strains.

1.6 Cloning of Human alpha-2,6 sialyltransferase cDNA encoding human alpha-2,6 sialyl-transferase (accession number: NM_003032) was cloned into the plant expression vector pRT101 (Toepfer et al. (1987) Nucl Acids Res 15, 5890). The cDNA coding for human alpha-2,6 sialyltransferase was amplified by PCR using primer MOB 636 (5'-GCTGAGCTCGA-ACACATCTTCATTATG-3') (SEQ ID NO 13) and primer MOB637 (5'-GATGGATCCTTAG-CAGTGAATGGTCCG-3') (SEQ ID NO 14). The amplification product was cut with SacI and BamHI and cloned into pRT101. In the resulting construct alpha-2,6 sialyltransferase was under regulation of the 35S promoter and 35S terminator—together termed as expression construct. For transformation procedure the expression construct was excised with Hind III. The linearised fragment containing alpha-2,6 sialyltransferase under regulation of the 35S promoter and 35S terminator was used for transformation of *Physcomitrella patens* strains.

1.7 Transformation Screening and Analysis

Transformation of different *Physcomitrella* strains was performed by PEG-mediated direct DNA transfer by simultaneous co-transformation of the constructs described in 1.1-1.6.

By using the appropriate primers for each construct (1.1: human UDP-N-acetylglucosamine-2-epimerase/N-acetylmanno-samine-6-kinase under regulation of Pp tub3 promoter and Pp alpha 1,3 fucosyltransferase terminator with primer MOB1214 (5'-GCAGGCTGCCCTTCCTAT-3') (SEQ ID NO 15) and primer MOB1196 (5'-AGAGATATTCTCCT-TCAC-3') (SEQ ID NO 16); 1.2: human N-acetylneuraminic acid phosphate synthase under regulation of 35S promoter and 35S terminator with primer MOB1213 (5'-ATGC-CGCTGGAGCTGGAG-3') (SEQ ID NO 17) and primer MOB1212 (5'-GTGTCTCCAGATCCAAC-3') (SEQ ID NO 18); 1.3: human CMP-N-acetylneuraminic acid synthase under regulation of 35S promoter and 35S terminator with primer MOB835 (5'-ATCGAATTCATGGACTCGGTG-GAGAAGGG-3') (SEQ ID NO 9) and primer MOB1153 (5'-TCGGTCACTTCACGAACT-3') (SEQ ID NO 19); 1.4: human CMP-sialic acid transporter under regulation of 35S promoter and 35S terminator with primer_MOB638 (5'-GTCGAGCTC-GGAACCATGGCTGCCCGA-3') (SEQ ID NO 11) and MOB1151 (5'-CAGATCGGAGCCAAGT-TCTG-31) (SEQ ID NO 20); 1.5: human beta-1,4 galactosyltransferase as described by Huether et al. ((2005) Plant Biol 7, 292-299); 1.6: human alpha-2,6 sialyltransferase under regulation of 35S promoter and terminator with primer MOB 636 (5'-GCTGAGCTCGAACACATCTTCATTATG-3') (SEQ ID NO 13) and primer MOB1149 (5'-CGCTGACAGCACAA-CAGC-3') (SEQ ID NO 21)), respectively, transgenic strains were identified by PCR on genomic DNA.

Strains transgenic for all constructs (1.1-1.6) were analysed in terms of sialic acids linked to N-glycans on glycoproteins as well as for free sialic acid (NeuAc5) and CMP-sialic acid (CMP-NeuAc5).

The analysed bryophyte strains transgenic for all constructs (1.1-1.6) showed significant content of sialic acids derived from N-glycans of glycoproteins.

High amounts (up to 100 nmol/g) of free sialic acid were detected. The sialic acid in the transgenic bryophytes was confirmed by MSMS analysis showing the identical spectrum compared to the standard and was not detected in the wild-type of *Physcomitrella patens*.

High yields of activated sialic acid (CMP-Neu5Ac) were detected in the transgenic bryophytes. In contrast CMP-Neu5Ac could not be detected in the wild-type of *Physcomitrella patens*.

The invention claimed is:

1. A transformed bryophyte cell that comprises six heterologous nucleotide sequences each operably linked to an exogenous promoter that drives expression in the bryophyte cell wherein said six nucleotide sequences encode six functional proteins that are expressed in the bryophyte cell, wherein said six functional proteins are a mammalian UDP-N-acetylglucosamine-2-epimerase/N-acetylmannosamine-6-kinase, a mammalian N-acetylneuraminic acid phosphate synthase (sialic acid synthase), a mammalian CMP-N-acetylneuraminic acid synthase, a mammalian CMP-sialic acid transporter, a galactosyltransferase, and a mammalian sialyltransferase.

2. A transformed bryophyte cell according to claim 1, wherein said nucleic acid sequences are mammalian nucleic acid sequences.

3. A transformed bryophyte cell according to claim 1, wherein said galactosyltransferase is a beta-1,4 galactosyltransferase.

4. A transformed bryophyte cell according to claim 1, wherein said sialyltransferase is selected from the group consisting of an alpha-2,6 sialyltransferase, an alpha 2,3 sialyltransferase, and a human alpha-2,6 sialyltransferase nucleotide sequence.

5. A transformed bryophyte cell according to claim 1, in which fucosyltransferase and/or xylosyltransferase activity is significantly reduced or eliminated.

6. A transformed bryophyte cell according to claim 1 that is a *Physcomitrella patens* cell.

7. A transformed bryophyte cell according to claim 6 that is comprised in protonema tissue of *Physcomitrella patens*.

8. A plant host cell containing six heterologous polynucleotide sequences each encoding a functional polypeptide, wherein said functional polypeptides are a mammalian UDP-N-acetylglucosamine-2-epimerase/N-acetyl-mannosamine-6-kinase, a mammalian N-acetylneuraminic acid phosphate synthase (sialic acid synthase), a mammalian CMP-N-acetylneuraminic acid synthase, a mammalian CMP-sialic acid transporter, a galactosyltransferase, and a mammalian sialyltransferase.

9. A host cell according to claim 8 which is a bryophyte cell.

10. A host cell according to claim 9, which is comprised in a bryophyte, or a bryophyte part, or an extract or derivative of a bryophyte or in a bryophyte cell culture.

11. A bryophyte plant or bryophyte tissue comprising a bryophyte cell as defined in claim 9.

12. A transformed bryophyte cell according to claim 2, wherein said mammalian nucleic acid sequences are human nucleic acid sequences.

13. A transformed bryophyte cell according to claim 3, wherein said beta-1,4 galactosyltransferase is a human beta-1,4 galactosyltransferase.

* * * * *

SEQUENCE LISTING

<160> NUMBER OF SEQ ID NOS: 21

<210> SEQ ID NO 1
<211> LENGTH: 794
<212> TYPE: DNA
<213> ORGANISM: Physcomitrella patens

<400> SEQUENCE: 1
cggtgatccc gttttcatat cagtgtatta tcatcagtga ctgcatattg acacccaatt    60
ctgatgattt tttatttttt attttttatt tttttggta tggttacatg cttttcagag   120

-continued

```
gtttctatgc cgctgagtat tttcctgaat cgcgaggtgt gacaggttat ctgcgccgtc    180
cacccaatat tttatgatga gtcgatgatt cgtgagacta atctagctta acctttttct    240
tactggcaag tcaaaattga gtttaaaata tttcagtatc ctgttagtaa tttcagacac    300
atgtattcta tgtctcatac tctttacgtg aaagttcaac tgacttatat tttgtcgttt    360
ttctgtagat cactgtttta gcgcatacaa agacaattgt ctaaatattt ttaaagaagg    420
tgatatttta ttataagata gaagtcaata tgttttttg  ttatgcacat gacttgaata    480
aaataaattt ttttgttaga tttaaatact ttttgaatta tagctttgtt gaaattaagg    540
aatttatatt cataagaagc tactcgaaca aatttacaaa gagaacattt gataagtaaa    600
agtaattaaa agttttttt  aatttaaaaa gattaatttt tattaataag aagaacttgg    660
aaagttagaa aaatatttaa ctttaaaaat taagaaaaca aggcaaaact ttaatttaca    720
aatacttaat gtagattaat tttcttatta tatattagca caaattatca ttatgtgata    780
ttttatgtta ttgt                                                      794

<210> SEQ ID NO 2
<211> LENGTH: 35
<212> TYPE: DNA
<213> ORGANISM: Artificial
<220> FEATURE:
<223> OTHER INFORMATION: Primer MoB558

<400> SEQUENCE: 2
gttccgcggt gatcccgttt tcatatcagt gtatt                              35

<210> SEQ ID NO 3
<211> LENGTH: 36
<212> TYPE: DNA
<213> ORGANISM: Artificial
<220> FEATURE:
<223> OTHER INFORMATION: Primer MoB557

<400> SEQUENCE: 3
tttgagctct acgtaacaat aacataaaat atcaca                             36

<210> SEQ ID NO 4
<211> LENGTH: 30
<212> TYPE: DNA
<213> ORGANISM: Artificial
<220> FEATURE:
<223> OTHER INFORMATION: Primer MOB1108

<400> SEQUENCE: 4
gatggatcca ttgccaatgt attgattggc                                    30

<210> SEQ ID NO 5
<211> LENGTH: 41
<212> TYPE: DNA
<213> ORGANISM: Artificial
<220> FEATURE:
<223> OTHER INFORMATION: Primer MOB1124

<400> SEQUENCE: 5
gttatttcca ttcttctcca tcttcgctaa ggatgatcta c                       41

<210> SEQ ID NO 6
<211> LENGTH: 27
<212> TYPE: DNA
<213> ORGANISM: Artificial
<220> FEATURE:
<223> OTHER INFORMATION: Primer MOB1125
```

-continued

```
<400> SEQUENCE: 6
gtctctagac tagtagatcc tgcgtgt                                          27

<210> SEQ ID NO 7
<211> LENGTH: 30
<212> TYPE: DNA
<213> ORGANISM: Artificial
<220> FEATURE:
<223> OTHER INFORMATION: Primer MOB785

<400> SEQUENCE: 7
ggcctgcaga tgccgctgga gctggagctg                                       30

<210> SEQ ID NO 8
<211> LENGTH: 34
<212> TYPE: DNA
<213> ORGANISM: Artificial
<220> FEATURE:
<223> OTHER INFORMATION: Primer MOB786

<400> SEQUENCE: 8
gccggatcct taagacttga ttttttgcc atga                                   34

<210> SEQ ID NO 9
<211> LENGTH: 29
<212> TYPE: DNA
<213> ORGANISM: Artificial
<220> FEATURE:
<223> OTHER INFORMATION: Primer MOB835

<400> SEQUENCE: 9
atcgaattca tggactcggt ggagaaggg                                        29

<210> SEQ ID NO 10
<211> LENGTH: 35
<212> TYPE: DNA
<213> ORGANISM: Artificial
<220> FEATURE:
<223> OTHER INFORMATION: Primer MOB836

<400> SEQUENCE: 10
tgaggatccc tattttttggc atgaattatt aacct                                35

<210> SEQ ID NO 11
<211> LENGTH: 28
<212> TYPE: DNA
<213> ORGANISM: Artificial
<220> FEATURE:
<223> OTHER INFORMATION: Primer MOB638

<400> SEQUENCE: 11
gtcgagctcg gaaccatggc tgccccga                                         28

<210> SEQ ID NO 12
<211> LENGTH: 28
<212> TYPE: DNA
<213> ORGANISM: Artificial
<220> FEATURE:
<223> OTHER INFORMATION: Primer MOB639

<400> SEQUENCE: 12
atcggatcct cacacaccaa taactctc                                         28

<210> SEQ ID NO 13
```

```
<211> LENGTH: 27
<212> TYPE: DNA
<213> ORGANISM: Artificial
<220> FEATURE:
<223> OTHER INFORMATION: Primer MOB636

<400> SEQUENCE: 13
gctgagctcg aacacatctt cattatg                                         27

<210> SEQ ID NO 14
<211> LENGTH: 27
<212> TYPE: DNA
<213> ORGANISM: Artificial
<220> FEATURE:
<223> OTHER INFORMATION: Primer MOB637

<400> SEQUENCE: 14
gatggatcct tagcagtgaa tggtccg                                         27

<210> SEQ ID NO 15
<211> LENGTH: 18
<212> TYPE: DNA
<213> ORGANISM: Artificial
<220> FEATURE:
<223> OTHER INFORMATION: Primer MOB1214

<400> SEQUENCE: 15
gcaggctgcc cttcctat                                                   18

<210> SEQ ID NO 16
<211> LENGTH: 18
<212> TYPE: DNA
<213> ORGANISM: Artificial
<220> FEATURE:
<223> OTHER INFORMATION: Primer MOB1196

<400> SEQUENCE: 16
agagatattc tccttcac                                                   18

<210> SEQ ID NO 17
<211> LENGTH: 18
<212> TYPE: DNA
<213> ORGANISM: Artificial
<220> FEATURE:
<223> OTHER INFORMATION: Primer MOB1213

<400> SEQUENCE: 17
atgccgctgg agctggag                                                   18

<210> SEQ ID NO 18
<211> LENGTH: 17
<212> TYPE: DNA
<213> ORGANISM: Artificial
<220> FEATURE:
<223> OTHER INFORMATION: Primer MOB1212

<400> SEQUENCE: 18
gtgtctccag atccaac                                                    17

<210> SEQ ID NO 19
<211> LENGTH: 18
<212> TYPE: DNA
<213> ORGANISM: Artificial
<220> FEATURE:
<223> OTHER INFORMATION: Primer MOB1153

<400> SEQUENCE: 19
```

```
tcggtcactt cacgaact                                                    18

<210> SEQ ID NO 20
<211> LENGTH: 20
<212> TYPE: DNA
<213> ORGANISM: Artificial
<220> FEATURE:
<223> OTHER INFORMATION: Primer MOB1151

<400> SEQUENCE: 20
cagatcggag ccaagttctg                                                  20

<210> SEQ ID NO 21
<211> LENGTH: 18
<212> TYPE: DNA
<213> ORGANISM: Artificial
<220> FEATURE:
<223> OTHER INFORMATION: Primer MOB1149

<400> SEQUENCE: 21
cgctgacagc acaacagc                                                    18
```